Figure 1:
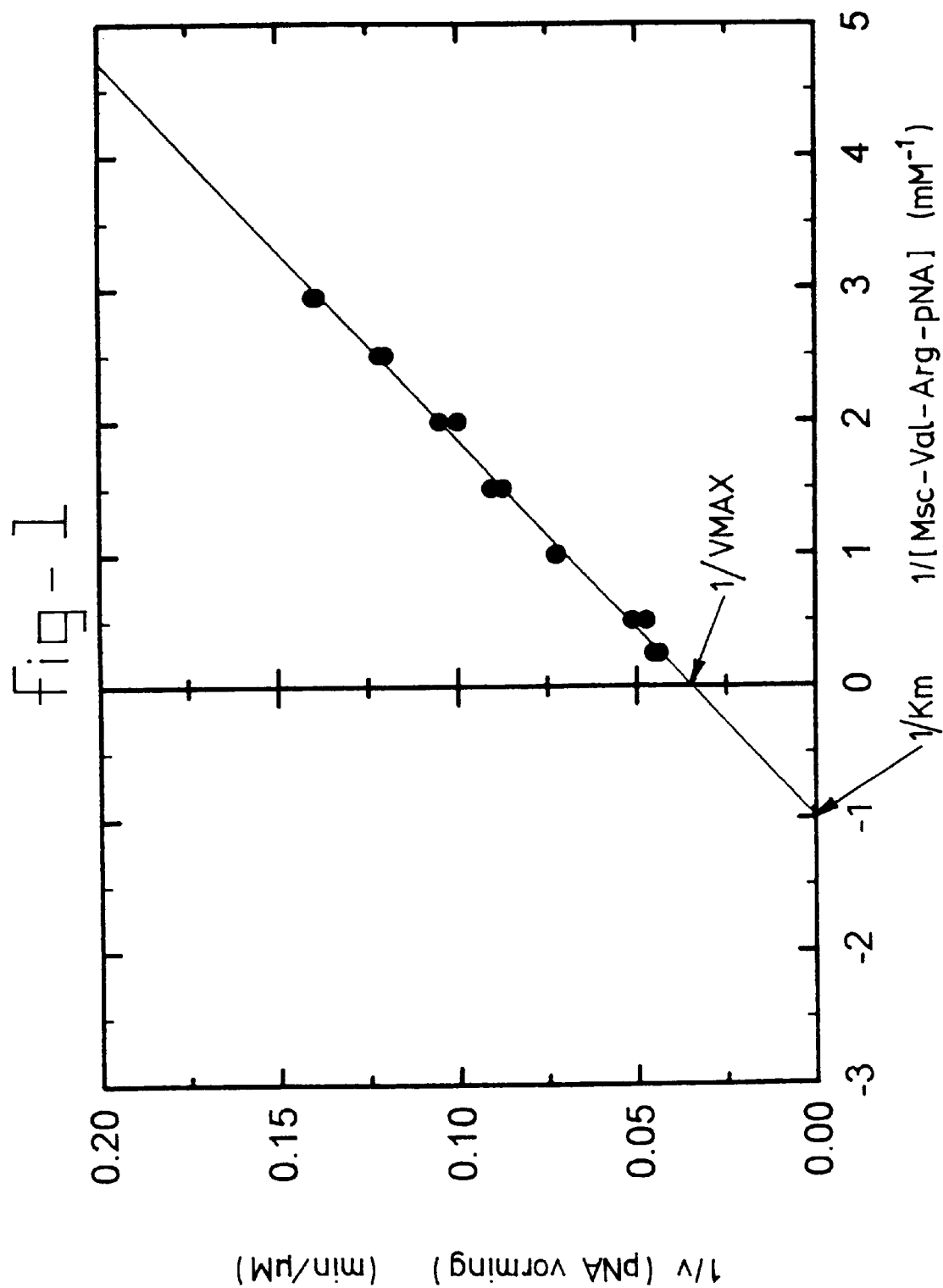

United States Patent [19]
Wagenvoord et al.

[11] Patent Number: 6,140,062
[45] Date of Patent: Oct. 31, 2000

[54] METHOD OF DETERMINING THE HEPARIN CONTENT

[75] Inventors: Robert Johan Wagenvoord; Hendrik Coenraad Hemker, both of Maastricht, Netherlands

[73] Assignee: Universiteit Maastricht, Maastricht, Netherlands

[21] Appl. No.: 09/254,046

[22] PCT Filed: Jun. 26, 1998

[86] PCT No.: PCT/NL98/00373

§ 371 Date: Mar. 1, 1999

§ 102(e) Date: Mar. 1, 1999

[87] PCT Pub. No.: WO99/00515

PCT Pub. Date: Jan. 7, 1999

[30] Foreign Application Priority Data

Jun. 27, 1997 [NL] Netherlands ............... 1006429

[51] Int. Cl.[7] .................... C12Q 1/38; C12Q 1/56; C07C 103/52; G01N 33/48; G01N 31/14
[52] U.S. Cl. .................... 435/7.1; 435/7.4; 435/4; 435/13; 435/23; 435/24; 435/968; 435/805; 436/69; 436/166; 436/169; 436/170; 530/331; 530/802; 260/112.5; 422/56; 422/57; 422/60; 422/61
[58] Field of Search ............... 435/7.1, 7.4, 4, 435/13, 23, 24, 968, 805; 436/69, 166, 169, 170; 438/13; 195/99, 103.5 R; 260/112.5; 23/230 B; 356/445, 446, 317, 318, 417; 422/56, 57, 60, 61; 427/2; 530/331, 802

[56] References Cited

U.S. PATENT DOCUMENTS

| | | | |
|---|---|---|---|
| 4,067,777 | 1/1978 | Innerfield et al. | 195/103.5 |
| 4,070,245 | 1/1978 | Svendsen | 195/99 |
| 4,169,015 | 9/1979 | Ekenstam et al. | 435/13 |
| 4,216,142 | 8/1980 | Ali | 260/112.5 |
| 4,221,706 | 9/1980 | Ali et al. | 260/112.5 |
| 4,520,100 | 5/1985 | Nagasawa et al. | 435/13 |
| 4,543,335 | 9/1985 | Sommer et al. | 436/69 |
| 4,622,389 | 11/1986 | Nagasawa et al. | 530/331 |
| 5,308,755 | 5/1994 | Nesheim et al. | 435/7.4 |

OTHER PUBLICATIONS

Ten Cate H et al. "Automated amidolytic method for determining heparin, a heparinoid, and a low molecular weight heparin fragment based on their anti–factor XA activity" Clin Chem 30 (6). 1984 pp. 860–864.

Van Putten J et al. "Automated determination of heparin with chromogenic substrates" Hemostasis 14 (2). 1984 pp. 184–194.

H. Ten Cate et al., "Automated amidolytic Method for Determining Heparin a Heparinoid and a Low Molecular Weight Heparin Fragment Based on Their Antifactor XA EC–3.4.21.6 Activity", *Clin Chem 30*, No. 6, 1984, pp. 860–864.

J. Van Putten et al., "Automated Determination of Heparin With Chromogenic Substrates", *Haemostasis 14*, No. 2, 1984, pp. 184–194.

*Primary Examiner*—Christopher L. Chin
*Assistant Examiner*—Lisa V. Cook
*Attorney, Agent, or Firm*—Young & Thompson

[57] ABSTRACT

In a method of determining heparin content, a known amount of thrombin (FIIa) or activated coagulation factor X (FXa) is added to a mixture which comprises a known concentration of chromogenic substrate (S), a known concentration of antithrombin (AT) and a sample having an unknown heparin concentration. The amount of FIIa or FXa is chosen such that at most 20%, of the S present is reacted during the period which the AT needs to deactivate all the FIIa or FXa present. The final concentration of the reacted chromogenic substrate p-nitroanilide ($[pNA]_{final}$) is determined after completion of the reactions, and the $[pNA]_{final}$ is used to determine the rate constant ($k_{dec}$) of the reaction of FIIa or FXa with AT using the relationship:

$$k_{dec} = \frac{k_{cat}}{Km} * [S] * \frac{1}{[pNA]_{final}} \ln \frac{[AT]}{[AT] - [E]}. \quad (1)$$

The heparin concentration in the sample can then be determined using the value of $k_{dec}$ from a predetermined calibration curve of $k_{dec}$ against heparin concentration.

5 Claims, 2 Drawing Sheets

METHOD OF DETERMINING THE HEPARIN CONTENT

The present invention relates to a method of determining the heparin content, in particular in plasma.

The coagulation factors X and II play an important part in the blood coagulation mechanism. The intrinsic and extrinsic systems of the blood coagulation mechanism meet in coagulation factor X. Under the influence of the activated factor X (FXa), factor II (prothrombin) is activated to form IIa (FIIa or thrombin). Thrombin then catalyses the conversion of fibrinogen into fibrin, as a result of which the actual blood coagulation occurs.

An important inhibitor of both FXa and FIIa is anti-thrombin III (AT), a protein which occurs in blood plasma and which deactivates FXa and FIIa by concomitantly forming a complex in an irreversible manner. AT thus inhibits the blood coagulation. It is known that heparin intensifies the deactivating action of AT by increasing the reaction rate with which AT forms an irreversible complex with FXa or FIIa.

Heparin is a mixture of polysaccharides having molecular weights which vary from 2000 to more than 40,000. It is known that active heparin is composed of two different types of active molecules: heparin molecules having a molecular weight which is higher than 5400 daltons (ACLM) and heparin molecules having a molecular weight of 5400 daltons or less (BCLM). The ACLM variant has both anti-FXa and anti-FIIa activity, while the BCLM variant has only anti-FXa activity. For this reason, the ratio between anti-FIIa activity and anti-FXa activity depends on the distribution of the polysaccharide chains in the heparin mixture.

The object of the present invention is therefore, inter alia, to provide a method with which it is possible to determine both the total heparin content and the separate contents of the ACLM and BCLM variants.

Methods of determining the heparin content of samples are known. Examples are the anti-thrombin test, the anti-FXa test, a test in which the activated partial thromboplastin time (APTT) is measured and various tests in which the decomposition of FXa or FIIa is measured. The results of said tests are often influenced by random variations in the plasma samples. For this reason, a calibration against a standard amount of heparin is necessary for every collection of plasma samples. In these methods, it is assumed that the result of the test with the standard will vary in the same way as with the samples to be tested. However, this is not always the case. An important cause of this is the fact described above that heparin is composed of two different types of active molecules. The ratio between anti-FIIa and anti-FXa activities is dependent on the distribution of the polysaccharide chains in the heparin. The anticoagulation action is dependent on the amount of anti-FIIa activity present. Because the anti-FIIa to anti-FXa activity ratio varies for each sample and for each sample preparation and is also dependent on the type of heparin and the time after which measurement is made, the result of a test which makes no distinction between ACLM and BCLM may result in incorrect interpretations of the test results. Various tests react differently to variations in the ratio between anti-FIIa activity and anti-FXa activity and it is therefore difficult to draw conclusions about the thrombotic behaviour of a patient.

The object of the present invention is therefore also a method of determining the heparin content in a sample in which a distinction can be made between the two types of heparin molecules mentioned above.

Moreover, U.S. Pat. No. 5,308,755 discloses a method of determining the heparin concentration in which a sample having an unknown heparin concentration is mixed with AT and a substrate for factor Xa or thrombin. Factor Xa or thrombin is then added to the sample in such a way that the enzyme is deactivated by the AT and that a portion of the substrate is converted into a product whose concentration can be determined.

According to said document, substrates having a high affinity for the enzyme, such as S2238 and S2222, are used. As a result, it takes a relatively long time before the final level of the measurement is reached. In addition, it is not possible with this method to measure the rate constant of enzyme inhibition by AT and no conclusion can therefore be drawn about the activity of the heparin.

The object of the present invention is therefore, moreover, to provide a method of determining the activity of heparin in a sample which can be performed relatively rapidly and simply and which provides an absolute result.

This and other objects are achieved with the method according to the invention.

FIG. 1: shows the rate of hydrolysis of Msc-Val-Arg-pNA measured as a function of the concentration of FIIA at 37° C.

Figure 2A:
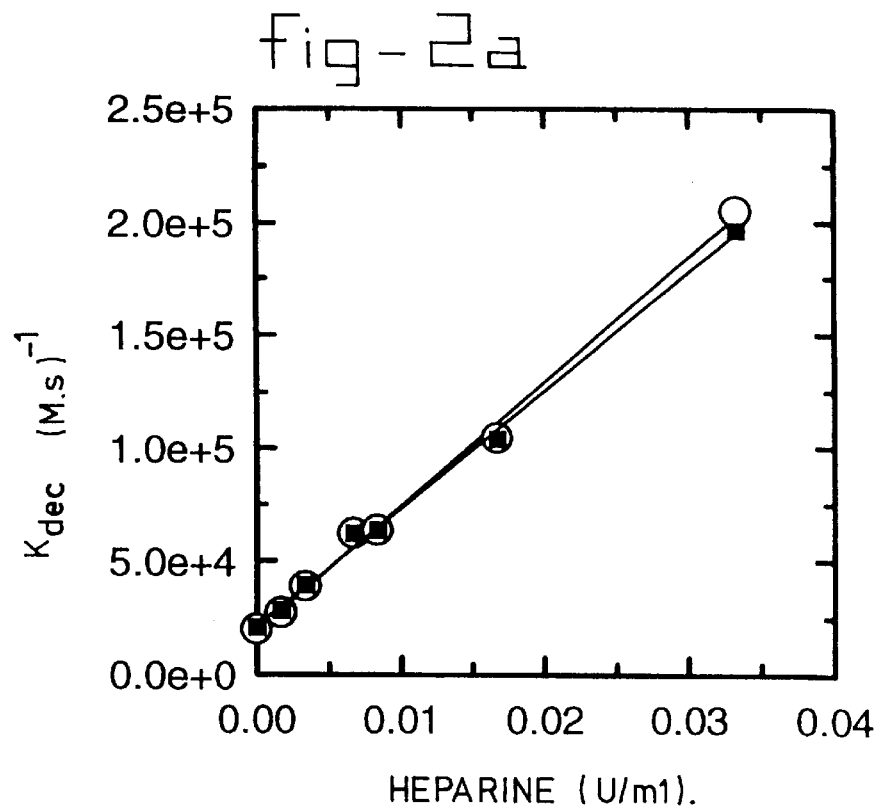
Figure 2B:
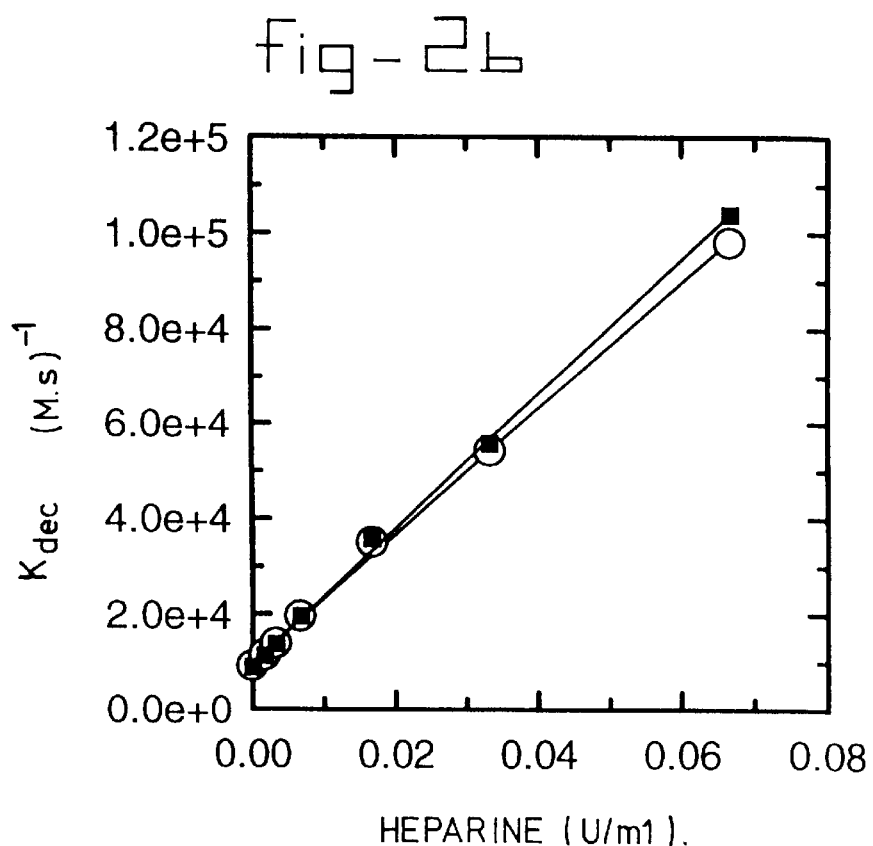

FIGS. 2a–2b: show calibration curves determined by measuring both anti-FIIa activity and anti-FXa activity.

The invention therefore relates to a method of determining the heparin content, which method comprises the following steps:

(a) adding a known amount of thrombin (FIIa) or activated coagulation factor X (FXa) to a mixture which comprises a known concentration of chromogenic substrate (S), a known concentration of antithrombin (AT) and a sample having an unknown heparin concentration, the amount of FIIa or FXa being chosen such that at most 20%, preferably at most 10%, of the S present is reacted during the period which the AT needs to deactivate all the FIIa or FXa present, (b) allowing the reactions which occur to proceed and determining the final concentration of the reacted chromogenic substrate ([pNA]$_{final}$) after completion of the reactions, (c) using the [pNA]$_{final}$ found to determine the rate constant ($k_{dec}$) of the reaction of FIIa or FXa with AT using the relationship:

$$k_{dec} = \frac{k_{cat}}{Km} * [S] * \frac{1}{[pNA]_{final}} \ln \frac{[AT]}{[AT] - [E]} \quad (1)$$

where:

$$Km = \text{Michaelis constant} = (k_{cat} + k_{-1})/k_1. \quad (2)$$

$k_{cat}$ = rate constant for the formation of the product pNA from the intermediate complex FIIa-S or FXa-S, $k_1$ = rate constant for the formation of an intermediate complex FIIa-S or FXa-S from FIIa or FXa and S, $k_{-1}$ = rate constant for the decomposition of the intermediate complex FXa-S or FIIa-S into FXa or FIIa and S,

[S] = initial concentration of the substrate,

[AT] = initial concentration of AT, and

[E] = initial concentration of FXa or FIIa, and (d) determining the heparin concentration in the sample using the value of $k_{dec}$ thus found from a predetermined calibration curve of $k_{dec}$ against heparin concentration, the temperature being virtually constant during the entire method.

A big advantage of the method according to the invention is that it is an end-point determination and is therefore time-independent. Many of the methods now known, on the other hand, are based on an instantaneous recording or series of instantaneous recordings from a progressive reaction. Another big advantage is that the heparin content of many samples can be measured simultaneously by making use of microtitre plates which contain a plurality of wells (generally 96). Furthermore, the method according to the invention has the big advantage that measurement can be performed directly on plasma. For this purpose, the plasma has only to be diluted with a suitable buffer.

In step (a) of the method according to the invention, a known amount of FIIa or FXa is added to a mixture of S, AT and the sample having an unknown heparin concentration. As a result of adding FIIa or FXa, two reactions occur:

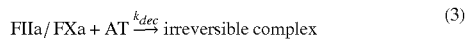

(3)

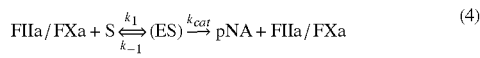

(4)

It is assumed that the conversion of S into pNA proceeds according to Michaelis-Menten kinetics. This means that S must be present in large excess with respect to FIIa/FXa so that $[S]+[(ES)] \approx [S]$. It is also assumed that the reaction of AT with FIIa or FXa is a second-order process. The Michaelis constant Km can be determined for reaction (4) (see relationship (2)). In order to guarantee a "constant"[S], at most only 20% of the S present must be converted, preferably at most 10%.

As already indicated above, it is known that heparin causes the reaction rate of the formation of the irreversible complex between FXa or FIIa, on the one hand, and AT, on the other hand, to increase substantially. It has been found that, if the correct conditions are created, the increase in the rate constant $k_{dec}$ is directly proportional to an increase in the heparin content. As a result, it is possible to measure the heparin concentration in a sample by determining $k_{dec}$.

Any known chromogenic substrate can be used as a chromogenic substrate, provided it has the correct kinetic properties. During hydrolysis of a suitable substrate, p-nitroanilide (pNA) is usually liberated. The amount of pNA liberated can readily be measured spectrophotometrically at a wavelength of 405 nm. However, there are in fact some practical considerations which make the use of certain substrates less suitable. The affinity of the substrate for the enzyme (i.e. FIIa or FXa) influences the heparin determination. In fact, the higher the affinity is, the longer it takes for all the enzyme to be deactivated by AT as a result of the formation of an irreversible complex. In other words, the use of a chromogenic substrate having a high affinity for FIIa or FXa means that it takes longer for the reaction (3) to proceed to completion. This means that the heparin measurement takes longer. Preferably, substrates are therefore used which have a none too high affinity for FIIa or FXa. Examples of very suitable substrates are (methylsulphonylethyl) oxycarbonylvalylarginine p-nitroanilide (Msc-Val-Arg-pNA) and malonyl-α-aminoisobutyrylarginine p-nitroanilide methylester monochloride (SQ68).

According to a preferred embodiment, diluted blood plasma is therefore used as the sample having an unknown heparin concentration in the method according to the invention. Preferably, the blood plasma is diluted in this case in such a way that the heparin concentration is situated in the central portion of the calibration curve. In practice this means that blood plasma has to be diluted 20 to 100 times, preferably 30 to 75 times. As a result, the heparin concentration in the final (i.e. diluted) sample is usually not more than 0.05 U/ml. The unit U/ml (units per ml) is a standard unit for specifying heparin concentrations and is used generally. The meaning of said unit and the manner in which it is determined is described in Merton R. E., Curtis A. D. and Thomas D. P., A comparison of heparin potency estimates obtained by activated partial thromboplastin time and British pharmacopoeial assays, Thromb. Haemost. 1985; 53:116–117.

In step (b) of the present method, the above-described reaction (3) is first of all allowed to proceed. Once said reaction is complete, reaction (4) will also no longer proceed. Usually the amounts of the reactants are chosen in such a way that reaction (3) is complete within 30 minutes, although a longer reaction time would yield equally good results. The reason why the reaction must preferably not last too long is the fact that the complete heparin determination must be capable of being performed within a time interval which is acceptable in practice. After reaction (3) has proceeded to completion and reaction (4) has therefore also stopped, the final concentration of the reacted chromogenic substrate is determined. Said reacted substrate is usually obtained by hydrolysis of the original substrate and can be determined spectrophotometrically. As has already been stated above, the chromogenic substrate is hydrolysed by FIIa or FXa, in which process p-nitroanilide (pNA) is liberated. The final concentration of pNA, $[pNA]_{final}$, can in fact readily be determined spectrophotometrically at a wavelength of 405 nm. This is generally known.

In step (c), the rate constant of the reaction of FIIa or FXa with AT ($k_{dec}$) is then determined with the $[pNA]_{final}$ thus found using the abovementioned relationship (1). The kinetic constants $k_{cat}$ and Km of the enzymatic hydrolysis of the chromogenic substrate can be determined from the so-called Lineweaver-Burk plot, in which the reciprocal substrate concentration (1/[S], along the abscissa) is plotted against the reciprocal rate at which pNA is formed (1/v, along the ordinate). The straight line intersects the abscissa at 1/Km, so that Km can readily be determined. The straight line intersects the ordinate at $1/v_{max}$, where $v_{max}=k_{cat}*[E]$ and [E] is the initial concentration of FIIa or FXa. The value of $k_{cat}$ is obtained by reading off $v_{max}$ from the figure and dividing by the known [FIIa] or [FXa]. All this is known. Because [S], [AT] and [E] are known, ln[AT]/([AT]-[E]) can be calculated. As stated, $[pNA]_{final}$ can be measured spectrophotometrically.

In step (d), the heparin concentration in the sample is determined using the value found for $k_{dec}$ from a predetermined calibration curve of $k_{dec}$ against heparin concentration. The calibration curve (i.e. calibration line) can be plotted in a manner known per se. When plotting the calibration curve, the same reactants should be used which are also used for the test itself. In this way, the accuracy of the test is in fact optimal. The calibration curve is preferably plotted in a region of the heparin concentration which is such that the pNA concentration to be measured is strongly dependent on the heparin concentration. In practice, it has been found that the measurement of the $k_{dec}$ of the FIIa deactivation by AT has a good reliability if the $k_{dec}$ is less than 200,000 $(Ms)^{-1}$ and preferably less than 100,000 $(Ms)^{-1}$. The measurement of the $k_{dec}$ of the FXa deactivation by AT has been found to be quite reliable at a $k_{dec}$ of less than 100,000 $(Ms)^{-1}$, preferably less than 50,000 $(Ms)^{-1}$. These limits determine the concentration range in which heparin measurements yield good results. For standard heparin, an anti-FIIa test appears to yield very good results if the heparin concentration range is 0–0.04 U/ml and, preferably, 0–0.02 U/ml. For an anti-FXa measurement, a concentration range of 0 to 0.08 U/ml, preferably 0 to 0.04 U/ml can be used particularly satisfactorily for plotting the calibration curve. It goes without saying that the sample is also preferably diluted in such a way that its heparin concentration is situated in the same region as that for which the calibration curve has been recorded. The best results are therefore obtained if the sample is diluted in such a way that the heparin concentration is between 0 and 0.04 U/ml.

Because the various reaction rates and rate constants are dependent on temperature, it is important that the temperature is virtually constant during all the steps of the method.

In order to obtain an indication of the concentrations of the separate ACLM and BCLM variants of heparin, the method according to the invention can be performed in such a way that the steps (a) to (d), inclusive, are performed separately with FXa and with FIIa. In this case, anti-FIIa activity is present in heparin fractions having a molecular weight of more than 5400 daltons (ACLM variant). Anti-FXa activity is encountered in heparin fractions having a molecular weight of 2800 daltons and higher. For both the anti-FIIa activity and the anti-FXa activity, the activity is strongly dependent on the size of the heparin molecules. Since heparin is a mixture of molecules of various sizes, the amounts of the ACLM and BCLM variants cannot readily be determined by measuring only the anti-FIIa and the anti-FXa activities of a sample. The anti-FIIa activity/anti-FXa activity ratio decreases, however, as the molecular weight of the heparin molecules becomes smaller. Below 5400 daltons this ratio is zero (no anti-FIIa activity), while it has been found that, above 8000 daltons, said ratio is approximately 3.

The invention is illustrated by reference to the following example.

EXAMPLE

The kinetic constants $k_{cat}$ and Km of the hydrolysis of the chromogenic substrate Msc-Val-Arg-pNA by human FIIa were determined at 37° C. For this purpose, the rate of hydrolysis of Msc-Val-Arg-pNA was measured as a function of the concentration of FIIa at said temperature. The results are shown in Table 1 and in FIG. 1.

TABLE 1

| | | | | Rates of hydrolysis | |
|---|---|---|---|---|---|
| Exp. | 5 mM S ($\mu$l) | BOA ($\mu$l) | 4.30 $\mu$m FIIa ($\mu$l) | Rate of hydrolysis ($\mu$M/min) | |
| 1 | 480 | 60 | 60 | 21.8 | 22.7 |
| 2 | 240 | 300 | 60 | 21.0 | 19.4 |
| 3 | 120 | 420 | 60 | 13.8 | 13.7 |
| 4 | 80 | 460 | 60 | 11.4 | 11.0 |
| 5 | 60 | 480 | 60 | 9.9 | 9.5 |
| 6 | 48 | 492 | 60 | 8.1 | 8.3 |
| 7 | 40.8 | 499 | 60 | 7.2 | 7.1 |

The solutions used were a 5 mM solution of Msc-Val-Arg-pNA (=S), a buffer solution (BOA) which contains 175 mM NaCl, 50 mM tris HCl (pH 7.9) and 2 mg/ml of ovalbumine, and a 4.30 $\mu$M solution of purified human FIIa. The substrate concentration [S] was determined by measuring the optical density of the reaction mixture at 316 nm and dividing by a constant characteristic of S (=12900). The concentration of FIIa, FXa and AT can also be determined in this way, but measurement is then performed at 280 nm and division is by a constant (known) for each protein. Each rate of hydrolysis was measured twice by determining the pNA concentration spectrophotometrically for 60 seconds at 405 nm.

From FIG. 1, it can be inferred that the kinetic constant at 37° C. of the hydrolysis of Msc-Val-Arg-pNA by FIIa is given by:

$v_{max}$=28.38 $\mu$M/min, so that $k_{cat}$=1.117 s$^{-1}$, and
Km=1.011 mM.

In an analogous way, it was determined that the kinetic constants for the hydrolysis of Msc-Val-Arg-pNA by FXa had the following values:

$k_{cat}$=1.87 s$^{-1}$ and
Km=5.50 mM.

The calibration curves were then determined for measuring both the anti-FIIa activity and the anti-FXa activity. The results are shown in FIGS. 2a and 2b.

For this purpose, the determination of the anti-FIIa and anti-FXa activities of heparin was performed in two series of cuvettes. The reaction mixture (600 $\mu$l) contained 1.0 $\mu$M AT, 2 mM Msc-Val-Arg-pNA, heparin as specified in the figures and the buffer solution BOA as specified above. The reaction was performed at 37° C. and was started at t=0 by adding 500 nM FIIa (uppermost series of cuvettes) or 500 nM FXa (lowermost series of cuvettes). The optical density was measured at 405 nM every second for 25 minutes. The reaction constants $k_{dec}$ were determined by curve fitting (-o-) or calculated from the optical density after 25 minutes (-■-).

The determination of heparin in plasma samples can be performed in an analogous way. Plasma samples which contain heparin (0–1.5 U/ml) were diluted 33×in BOA. The reaction mixtures were then prepared by mixing 100 $\mu$l of diluted plasma, 100 $\mu$l of 3 $\mu$M AT+6 mM Msc-Val-Arg-pNA and 100 $\mu$l of 1.5 $\mu$M FIIa or FXa. After 25 minutes, the pNA concentration was measured spectrophotometrically (at 405 nm) and the $k_{dec}$ was calculated according to relationship (1). The heparin concentration of the diluted sample was then determined using the calibration curves from FIGS. 2a and 2b, after which the heparin concentration of the undiluted sample was calculated.

The results in terms of $k_{dec}$ and heparin concentration of the undiluted sample are shown in Table 2.

TABLE 2

| Heparin determination in in plasma | | | |
|---|---|---|---|
| Anti-FIIa activity | | Anti-FXa activity | |
| $k_{dec}$ (Ms)$^{-1}$ | Heparin (U/ml) | $k_{dec}$ (Ms)$^{-1}$ | Heparin (U/ml) |
| 20184 | 0 | 9319 | 0 |
| 44522 | 0.0047 | 14970 | 0.0043 |
| 75305 | 0.0106 | 23635 | 0.0108 |
| 96003 | 0.0145 | 33585 | 0.0183 |

What is claimed is:

1. Method of determining the heparin content, which method comprises the following steps:

(a) adding a known amount of thrombin (FIIa) or activated coagulation factor X (FXa) to a mixture which comprises a known concentration of chromogenic substrate (S), a known concentration of antithrombin (AT) and a sample having an unknown heparin concentration, the amount of FIIa or FXa being chosen such that at most 20%, of the S present is reacted during the period which the AT needs to deactivate all the FIIa or FXa present, (b) allowing the reactions which occur to proceed and determining the final concentration of the reacted chromogenic substrate p-nitroanilide ($[pNA]_{final}$) after completion of the reactions, (c) using the $[pNA]_{final}$ found to determine the rate constant ($k_{dec}$) of the reaction of FIIa or FXa with AT using the relationship:

$$k_{dec} = \frac{k_{cat}}{Km} * [S] * \frac{1}{[pNA]_{final}} \ln \frac{[AT]}{[AT]-[E]} \quad (1)$$

where:

*=a multiplication operation $Km$=Michaelis constant=$(k_{cat}+k_{-1})/k_1$, (2)

$k_{cat}$=rate constant for the formation of the product pNA from the intermediate complex FIIa-S or FXa-S, $k_1$=rate constant for the formation of an intermediate complex FIIa-S or FXa-S from FIIa or FXa and S, $k_{-1}$=rate constant for the decomposition of the intermediate complex FXa-S or FIIa-S into FXa or FIIa and S,

[S]=initial concentration of the substrate,
[AT]=initial concentration of AT, and
[E]=initial concentration of FXa or FIIa, and (d) determining the heparin concentration in the sample using the value of $k_{dec}$ thus found from a predetermined calibration curve of $k_{dec}$ against heparin concentration, the temperature being constant during the entire method.

2. Method according to claim 1, wherein the sample having an unknown heparin concentration is diluted blood plasma.

3. Method according to claim 2, wherein the blood plasma is diluted in such a way that the heparin concentration is at most 0.04 U/ml.

4. Method according to claim 1, wherein (methylsufonylethyl) oxycarbonylvalylarginine p-nitroanilide (Msc-Val-Arg-pNA) or malonyl-α-aminoisobutyrylarginine p-nitroanilide methylester monochloride (SQ68) is used as chromogenic substrate.

5. Method according to claim 1, wherein $[pNA]_{final}$ is determined spectrophotometrically at a wavelength of 405 nm.

* * * * *